United States Patent
Schramm

(10) Patent No.: US 9,651,463 B2
(45) Date of Patent: May 16, 2017

(54) APPARATUS AND METHOD FOR PRODUCING ANALYSIS SAMPLES

(71) Applicant: Fluxana GmbH & Co. KG, Bedburg-Hau (DE)

(72) Inventor: Rainer Schramm, Bedburg-Hau (DE)

(*) Notice: Subject to any disclaimer, the term of this patent is extended or adjusted under 35 U.S.C. 154(b) by 108 days.

(21) Appl. No.: 14/670,791

(22) Filed: Mar. 27, 2015

(65) Prior Publication Data

US 2015/0198511 A1 Jul. 16, 2015

Related U.S. Application Data

(63) Continuation-in-part of application No. PCT/EP2013/069099, filed on Sep. 16, 2013.

(30) Foreign Application Priority Data

Sep. 28, 2012 (DE) .......................... 10 2012 109 248

(51) Int. Cl.
*G01N 23/22* (2006.01)
*F27B 17/02* (2006.01)
(Continued)

(52) U.S. Cl.
CPC ............... *G01N 1/44* (2013.01); *F27B 14/02* (2013.01); *F27B 14/08* (2013.01); *F27B 17/02* (2013.01); *G01N 1/38* (2013.01); *G01N 23/2202* (2013.01); *G01N 23/2204* (2013.01); *F27D 2005/0075* (2013.01)

(58) Field of Classification Search
CPC .. B01L 3/04; F27B 17/02; F27B 14/08; F27B 2014/0831
See application file for complete search history.

(56) References Cited

U.S. PATENT DOCUMENTS 1,749,083 A * 3/1930 Morris .................... B22D 41/06
222/166
2,205,023 A * 6/1940 York ....................... B22D 41/06
294/28

(Continued)

FOREIGN PATENT DOCUMENTS

DE 589569 A 11/1933
DE 906 428 B 1/1954
(Continued)

*Primary Examiner* — David A Rogers
(74) *Attorney, Agent, or Firm* — Patricia Mathers; Jeffrey Joyce

(57) ABSTRACT

Apparatus for producing analysis samples for X-ray fluorescence spectroscopy that includes a crucible holder that supports a crucible with sample material and a casting dish that is provided underneath the crucible. The crucible is tiltably mounted in the crucible holder and the crucible holder along with crucible holder and the casting dish is handled as a single unit for loading and unloading the oven. The oven has a floor on which the crucible holder is positioned upright, and the portion of the floor receiving the crucible holder is designed as a turntable which imparts oscillating rotational motion to the crucible holder and crucible holder. The method entails placing the crucible with the sample material in the crucible holder while they are outside the oven and then placing entire crucible unit loosely in the oven.

16 Claims, 3 Drawing Sheets

(51) Int. Cl.
  *G01N 1/44* (2006.01)
  *F27B 14/02* (2006.01)
  *F27B 14/08* (2006.01)
  *G01N 1/38* (2006.01)
  *F27D 5/00* (2006.01)

(56) References Cited

U.S. PATENT DOCUMENTS

| | | | | |
|---|---|---|---|---|
| 2,444,461 A * | 7/1948 | Morey | ............ | B22D 41/06 |
| | | | | 248/137 |
| 3,451,794 A * | 6/1969 | Patterson | ............ | C03B 19/02 |
| | | | | 264/71 |
| 4,175,610 A * | 11/1979 | Zauhar | ............ | C30B 29/06 |
| | | | | 164/122.2 |
| 4,462,963 A * | 7/1984 | O'Brien | ............ | G01N 31/12 |
| | | | | 373/130 |
| 4,563,146 A * | 1/1986 | Kelly | ............ | B22D 41/06 |
| | | | | 164/157 |
| 4,609,392 A * | 9/1986 | Claisse | ............ | F27B 14/10 |
| | | | | 65/134.4 |
| 4,871,309 A * | 10/1989 | Chapman | ............ | G01N 1/44 |
| | | | | 432/156 |
| 5,178,508 A * | 1/1993 | Tauer | ............ | B01F 7/1605 |
| | | | | 248/129 |
| 5,269,827 A * | 12/1993 | Lenke | ............ | G01N 1/44 |
| | | | | 366/211 |
| 5,313,047 A * | 5/1994 | O'Brien | ............ | G01N 1/44 |
| | | | | 164/338.1 |
| 5,315,091 A * | 5/1994 | O'Brien | ............ | F27B 17/02 |
| | | | | 164/136 |
| 5,381,855 A * | 1/1995 | Mezger | ............ | B22D 39/026 |
| | | | | 164/136 |
| 5,393,190 A * | 2/1995 | Vickary | ............ | B65G 65/23 |
| | | | | 187/226 |
| 5,585,023 A * | 12/1996 | Beckley | ............ | F27B 17/02 |
| | | | | 219/386 |
| 5,985,674 A * | 11/1999 | Umezawa | ............ | G01N 33/20 |
| | | | | 148/508 |
| 7,232,489 B2 * | 6/2007 | Webb | ............ | B01L 9/50 |
| | | | | 117/208 |
| 7,736,586 B2 * | 6/2010 | Takahashi | ............ | H05B 6/34 |
| | | | | 266/233 |
| 7,775,257 B2 * | 8/2010 | Khan | ............ | B22D 41/015 |
| | | | | 164/136 |
| 8,075,693 B2 * | 12/2011 | Noh | ............ | C23C 14/12 |
| | | | | 118/726 |
| 8,210,000 B2 * | 7/2012 | Prossor | ............ | C03B 5/06 |
| | | | | 432/156 |
| 8,327,912 B2 * | 12/2012 | Terada | ............ | B22D 41/06 |
| | | | | 164/136 |
| 8,573,921 B2 * | 11/2013 | Waisanen | ............ | B66C 1/62 |
| | | | | 414/812 |
| 2008/0274031 A1 * | 11/2008 | Ito | ............ | C01B 33/037 |
| | | | | 423/350 |
| 2008/0314547 A1 * | 12/2008 | Khan | ............ | B22D 41/015 |
| | | | | 164/133 |

FOREIGN PATENT DOCUMENTS

| | | | | |
|---|---|---|---|---|
| DE | 1596729 A | | 4/1971 | |
| DE | 1648994 C3 | | 8/1971 | |
| DE | 2504918 A1 | | 8/1976 | |
| DE | 2806335 A1 | | 8/1978 | |
| DE | 3507493 A1 | | 9/1985 | |
| DE | 4242110 A1 * | | 6/1994 | ......... B22D 13/063 |
| DE | 10338886 A1 | | 3/2005 | |
| DE | 10 2010 037 866 A1 | | 3/2012 | |
| EP | 0501835 A2 | | 9/1992 | |
| EP | 0775906 A1 | | 5/1997 | |
| EP | 2270410 B1 | | 11/2011 | |
| GB | 2032076 A * | | 4/1980 | |
| JP | DE 19717380 A1 * | | 11/1997 | ............ C30B 15/10 |
| WO | 9706060 A1 | | 2/1997 | |

* cited by examiner

APPARATUS AND METHOD FOR PRODUCING ANALYSIS SAMPLES

BACKGROUND INFORMATION

Field of the Invention

The invention relates to apparatus for producing analysis samples for X-ray fluorescence spectroscopy, as well as a method for producing the same.

Discussion of the Prior Art

In X-ray fluorescence spectroscopy, the material to be analyzed is first melted in a crucible and then poured into a casting dish to form what is typically referred to in the field as a "pellet," "tablet," "button," or "bead" that is then used for the analysis. These buttons are typically quite small, about the size of a one-Euro or a two-Euro coin. The equipment is correspondingly small: the crucibles typically have a height of just a few centimeters, for example, approximately 3 to 5 cm, and a similar diameter. Hence, the amount of the material to be melted is in the range of several grams and at most several cubic centimeters. The crucibles could be designated as analysis sample crucibles, but, despite substantial differences to crucibles of the type used in steel mills, foundries, and similar production facilities, the simple term "crucible" is also used for these small crucibles that are used in laboratories for X-ray fluorescence spectroscopy.

The temperatures used to melt the sample materials are very high, ranging from 900 degrees C. to 1400 degrees C. As a result, the equipment obtaining samples for X-ray fluorescence spectroscopy is exposed to high temperature loads.

Crucibles are also used in production industries, for example, in steel mills, in foundries, etc., to produce large and small articles. In these cases, the mass of material to be melted is measured in the range of kilograms and possibly hundreds of kilograms, and the volume in many liters or possibly even cubic liters or cubic meters. The crucibles used for industrial production are typically so large, that they are not placed in the oven at all, but rather, the molten liquid material that is in the oven is poured outside the oven into crucibles or is melted directly in crucibles that are heatable, without the use of an oven. Because these types of crucibles are not placed in an oven, the entire crucible is not designed to be able to withstand the high temperatures that are used in melting operations; instead, just the surface that comes into contact with the molten material is coated with some heat-resistant material, such as a ceramic material. An external metal shell may be provided, but this does not have sufficient resistance to withstand the temperature of the molten material that is in the crucible, and particularly, cannot withstand the temperatures that exist in a melting oven that is used to produce the samples for X-ray fluorescence spectroscopy.

For these reasons, foundry or smelting apparatus that is used in the industrial processing of large volumes of material is, thus, unrelated to apparatus that is used to produce the samples for X-ray fluorescence spectroscopy.

In the production of analysis samples for X-ray fluorescence spectroscopy, the crucible is not setup outside the oven and filled outside the oven with molten sample material, and is also not the type of crucible that has a heat source that heats the sample material directly in the crucible. Rather, the crucible is placed in the oven and is passively heated by the temperature that exists in the oven. Thus, it is essential that a crucible used for analysis samples not just have a fire-resistant coating on the inside of the crucible where the molten material is, but that the entire crucible be able to withstand the high temperatures in the oven. For this reason, crucibles for analysis samples are made entirely of a material that is thermally resistant to the oven temperatures as well as chemically resistant to the sample material. An example of material for such crucibles is platinum or a platinum alloy.

Often in X-ray fluorescence spectroscopy, several crucibles, for example, two, four, or six crucibles, are placed together in one oven. The ovens used for this are often referred to as so-called tabletop devices, because they are so small, they can be placed on a laboratory table, for example. But even if the ovens are set up on the floor or are placed in a rack or cabinet, they are still referred to as tabletop devices, because of their small dimensions.

To produce the button, the molten sample material in the crucible is cast from the crucible into a casting dish. Typically, this operation is carried out inside the oven, in order to minimize the risk that the sample material cools prematurely. The casting dish, which is sometimes also referred to as a mold, is placed in the oven beneath the crucible, and has a concave shape that determines the shape of the button.

Flux or filler is typically added to the sample material as a filler, whereby this flux is frequently in the form of glass. The crucible is set in motion in the oven, in order to thoroughly mix the actual sample material with the filler materials within the crucible.

The use of stirrers in the crucible hasn't proven useful, for a variety of reasons. The conventional method is to set the complete crucible, including its crucible holder and the contents of the crucible, in motion. It is often problematic for practical reasons to do this, because of undesirably high wear on the crucible holder. If such a crucible holder breaks and has to be replaced, then the oven, which may normally have charges of two, four, or six crucibles, cannot be used for the duration of the repair, which results in a significant economic loss.

There are a number of causes for the sensitivity of the conventional crucible holder. For one, the oven used for X-ray fluorescence spectroscopy has an enclosed inner chamber and the temperatures in the oven are very high, as mentioned above. For another, the entire crucible holder with all the crucibles contained in it, is set in motion, in order to mix the sample materials. Also, the crucible holder with all of its crucibles is tiltably supported, so that all the crucibles can simultaneously be poured from the crucibles into the casting dishes beneath the crucibles. This simultaneous emptying is done to avoid a premature and undesired cooling of the samples, and, for this reason, the crucibles are not emptied one after the other.

For these reasons, the crucible used for X-ray fluorescence spectroscopy must satisfy very different conditions than those of crucibles used in industrial production. The conventional apparatus for X-ray fluorescence spectroscopy has lower temperature losses because of the enclosed chamber and, consequently, can be operated more economically and can also be operated with heaters that have a lower heat output than the gas burner that is typically used in industrial applications. Electric heaters, for example, may be used and that is an advantage for safety reasons. Also, the heating effect of a gas burner is concentrated on a small area, for example, on the crucibles. With the conventional X-ray fluorescence spectroscopy apparatus, a significantly more even temperature is provided in the entire closed inner chamber of the oven and, because of this, the crucible holders for the crucibles in X-ray fluorescence spectroscopy are subjected to higher thermal loading. The same applies for the drive elements of the crucible holder that are also provided inside the inner chamber of the oven. These drive elements are used to set the crucible holder along with all its crucibles in motion, the purpose of which is to thoroughly mix the sample materials in the crucibles. Having to repair these crucible holders is a relatively complex task and takes a correspondingly long time, because the oven has to be first cooled down before the crucible holder can be removed.

What is needed, therefore, are apparatus and a method in X-ray fluorescence spectroscopy of loading/unloading an oven that will provide the highest possible productivity level. What is further needed is a crucible holder that is robust enough to withstand the high temperatures of the ovens and has sufficient stability to be placed loosely in the oven. What is yet further needed are apparatus and method for producing samples for X-ray fluorescence spectroscopy with the shortest possible down times and cycle times.

BRIEF SUMMARY OF THE INVENTION

The inventive subject matter includes apparatus and a method for producing a sample to be analyzed with X-ray fluorescence spectroscopy. The inventive apparatus comprises a conventional oven, a crucible holder that can support one or more crucibles, and a corresponding number of casting dishes, a casting dish being placed beneath each crucible. The crucible holder is loaded with the crucible and the casting dish, and the sample material and filler filled into the crucible. These steps are done outside the oven. Then, the crucible, together with the casting dish and the crucible, is put into the oven, loosely placed on the oven floor, for the purpose of melting the sample material. In other words, the crucible holder, the crucible, and the casting dish are handled as a single unit. The ability to do this saves time loading and unloading the oven, because loading or unloading is done as a single step, rather than in separate steps to remove the crucible and then possibly the casting dish.

The contents of the crucible need to be thoroughly mixed with one another and this is accomplished by setting the crucible in motion. The oven has a means of setting the crucible holder in motion. This motion is transmitted to the one or more crucibles, to achieve the desired mixing of the crucible contents. Once melted, the molten sample material is poured from the crucible into the respective casting dish, while the crucible holder and crucible are still in the oven.

The crucible holder according to the invention is made of a high-temperature resistant material and has a rugged, simple construction that makes it extremely stable, i.e., it can withstand motion without leaning or falling over, and because of this, it able to be loosely placed within the oven. In other words, the crucible holder has such stability, that it may be placed in the oven and be set in a motion to effect a thorough mixing of the contents of the crucible, without requiring additional fixing devices to secure it in place.

The casting dish is a shallow mold for the button, and is provided in a casting dish support plate that is supported in a position that is beneath the crucible in the crucible holder. The crucible holder has a geometry that provides a positive locking fit for the casting dish support plate, such that the support plate is unable to shift in any horizontal direction, thereby ensuring that the casting dish is always in the proper position beneath the crucible for a precise pouring operation. The crucible is tiltably supported in the crucible holder above the casting dish, and the molten contents of the crucible are emptied into the casting dish by tilting the crucible in the crucible holder.

The embodiment of the crucible holder as a component separate from the oven enables a method of producing beads for X-ray fluorescence spectroscopy that has shorter cycle times and downtimes. Loading and unloading the crucible on the crucible holder outside the oven and then loading/unloading the oven by handling the crucible holder, crucible holder, and casting plate together as a single crucible unit, enables an almost continuous melting process. The term "crucible unit" as used hereinafter includes the crucible holder, the crucible, and the casting plate. For example, a second crucible unit may be prepared while a first crucible unit is in the oven undergoing the melting and pouring process. The preparation of the second crucible unit entails loading the crucible holder with a second crucible that contains unmelted sample material, and possibly loading a second, empty casting dish into the crucible holder. When the oven is opened, the second crucible unit can immediately be placed in the oven as soon as the first crucible unit has been removed. This method holds temperature losses in the opened oven to a minimum, because the oven is opened a shorter period of time, and overall the cycle time is shortened, too, because the use of additional crucibles and crucible holders that can be pre-loaded in advance of placement into the oven means that one doesn't have to wait for the crucible holder and the casting dish to cool down and be cleaned, before they can be loaded into the oven again.

The method according to the invention also means that downtime is eliminated in those cases in which a crucible holder becomes damaged and needs to be replaced. Spare crucible holders are available and the next crucible unit may be prepared and loaded into the oven, in the course of regular operation, while the damaged crucible holder is shunted off to the side for repair. The oven is regularly opened to withdraw the crucibles and replace them with new crucibles that are filled with the sample material. At the same time, the samples that have been poured into the casting dishes are also removed from the oven. The casting dishes are either emptied and placed back in the oven, or new, empty casting dishes are placed in the oven. While carrying out these steps that will be done in the regular course of operation, the crucible holder that has been loosely placed within the oven may be easily removed, so that the oven operations are interrupted by only a few additional seconds, after which they can proceed normally.

As mentioned above, the apparatus and the method of the present invention foresees that the crucible holder be placed loosely in the oven. "Loosely" in this context means that the crucible holder is placed in the oven without the use of latches or tie-downs or other fixing elements to secure the crucible holder within the oven. This means that the crucible holder is easily and quickly moved in and out of the oven. The crucible holder according to the invention, due to its own weight and/or geometry, is so stable, that even with a filled crucible, it is reliably stable against lifting forces or against falling over in the oven and, because of that, no additional fastening brackets or tools are required to secure the crucible holder in the oven. The assessment of this stability is particularly in view of the motions that are applied to the crucible unit to bring about a thorough mixing of the crucible contents.

Although not necessary when the crucible holder is used in the oven in its intended manner, it is possible that some additional means be used to secure the holder in the oven. These additional means may be guide tracks or something similar, that prevent the crucible holder from shifting in a horizontal direction. The crucible holder is still "loosely" arranged in the oven, in the sense that it is slid along or between the guide tracks, so that the crucible unit securely stands in place within the oven when the mixing motions are applied to the crucible unit, but loading/unloading the oven is still easily and quickly accomplished.

It is also possible that latches, which are pivotable or otherwise movable, may be automatically actuated. For example, a latch may be provided that is pivotably mounted and extends from the pivotable mount in a first direction. The latch has an actuating pin that extends in a second direction from the pivotable mount. When the crucible holder is pushed into the oven, it pushes against the actuating pin. Without having to actually handle the actuating pin or the latch, the latch is automatically swung about by the travel of the crucible holder into the oven and extends over or around a portion of the crucible holder, so that the holder is secured against lifting forces or against falling over within the oven. When removing the crucible holder from the oven in the reverse direction of travel, the latch is then automatically swung back by the crucible holder, so that it is just as uncomplicated to remove the crucible holder from the oven as if it had actually stood entirely unsecured within the oven.

The method according to the invention a single charge of the oven may include placing several crucible holders, each loaded with a crucible, into the oven together. The term "charge" or "oven charge" as used herein refers to the one or more crucible units that are placed at one time in the oven. It is advantageous to include a plurality of crucible units in a charge, because, if one crucible holder fails, then it can be easily and quickly replaced, as described above. Replacement of the crucible holder is simplified by the fact the crucible holder that has to be handled is relatively small, i.e., is constructed to carry a single crucible, rather than several crucibles. If, however, a replacement crucible holder is not available, then it is still feasible to operate the oven, because then only one of the crucible holders is missing from the normal oven charge, and the remaining crucible holders may still be processed. As a result, the total reduction in throughput is only reduced by the percentage represented by the one crucible holder that is missing from the charge.

Placing each individual crucible in its own crucible holder also means that variously constructed crucibles may be used without problem in the same oven charge, because each one is arranged in the oven in its own crucible holder. By contrast, a crucible holder that is set up for several crucibles inherently limits the type of crucible that may be used to one that will work with the particular crucible holder.

It may however, be advantageous, to support two or more crucibles in the same crucible holder. Removing the crucible holder from the oven makes it possible in this case to remove several crucibles at the same time and, when using a tilt actuator that works on all crucibles simultaneously, it is then also possible to simultaneously empty these several crucibles into their respective casting dishes. It is a further advantage, that the process of removing the crucibles and then loading a new charge into the oven is simplified by the fact that only a single crucible holder need be handled. This eliminates any difficulties that may arise trying to situate and handle more than one crucible holder at a time in the oven.

The fact that only a single crucible holder need be handled further reduces the amount of time during which the oven is open for loading/loading a charge of crucibles, and this has a positive effect on maintaining the desired temperature in the oven. This is ecologically and economically advantageous, because it reduces the time and energy need to re-heat the oven to temperature and also shortens the cycle time for producing the beads or buttons.

As mentioned above, the crucible is tiltably supported in the crucible holder, so that the entire crucible holder does not have to be tilted to empty the contents of the crucible into the casting dish. The crucible alone is tilted, while the crucible holder itself remains unchanged in its position. This has the advantage, that the design of the crucible holder may be kept particularly simple, because it does not have to be connected to a drive mechanism inside the oven that would enable tilting the crucible holder along with the crucible. Particularly when, as described above, the apparatus is such, that each crucible is placed in its own crucible holder, then various tilt actuators are possible, so that different types of crucibles, which are possibly constructed differently with regard to their tilt movement, are each held in a crucible holder adapted to the particular type of crucible.

A tilt handle is provided on the crucible, for the purpose of tilting the crucible about its tilt axis. Preferably, the tilt handle is placed horizontally opposite a pour spout of the crucible. Raising the tilt handle lowers the pour spout, so that the liquid molten sample material flows precisely out of the crucible into the casting dish. With the tilt handle, it is not necessary that the crucible be removed from the crucible holder for the pouring step, but rather, this handle just needs to be manipulated upward, in order to tilt and, thus, empty the crucible.

A simple and robustly constructed tilt actuator may be provided, such as, for example, a horizontally extending beam, to manipulate the tilt handle. The tilt actuator doesn't have to move the relatively high weight of the crucible and the crucible holder, and because of that, a small and inexpensive tilt actuator with a low drive performance may be sufficiently robust. If one or more crucible holders loaded with crucibles are arranged in the oven, or when one crucible holder loaded with several crucibles is arranged in the oven, the holder(s) may be so aligned, that the tilt handles on the crucibles extend out above the beam, i.e., the tilt actuator. When the samples in the crucibles are molten, only the actuator has to be raised, in order to simultaneously empty all the crucibles in a time-saving manner.

The crucible unit is subjected to motion in the oven. This is done to achieve a thorough mixing of the sample materials in the crucible(s). The motion is an oscillating rotational motion, thus, centrifugal forces are generated that act on the contents of the crucible. It is advantageous that the tilt support for the crucible be placed as far off-center as possible from the rotational axis of the crucible holder, to take advantage of the strongest possible centrifugal forces.

An oven that is advantageous to use with the apparatus and method according to the invention is one that has a floor that provides the mixing motion. One type of mixing motion that is particularly advantageous is a back-and-forth oscillating rotational motion, whereby each change in direction brings about a particularly strong mixing effect. For that reason, the floor or section of floor on which the crucible holder is placed is advantageously constructed as a turntable that is rotationally movable in an oscillating manner.

BRIEF DESCRIPTION OF THE DRAWINGS

The present invention is described with reference to the accompanying drawings, which are schematic illustrations only. In the drawings, like reference numbers indicate identical or functionally similar elements.

DETAILED DESCRIPTION OF THE INVENTION

The present invention will now be described more fully in detail with reference to the accompanying drawings, in which the preferred embodiments of the invention are shown. This invention should not, however, be construed as limited to the embodiments set forth herein; rather, they are provided so that this disclosure will be complete and will fully convey the scope of the invention to those skilled in the art.

The invention includes apparatus and a method for preparing a sample of material to be analyzed in X-ray fluorescence spectroscopy. The sample is initially solid material that is melted in a crucible, usually together with a flux or filler material, and cast into a mold or casting dish to form a flat button or tablet, and it is this button that is then analyzed.

Figure 1:
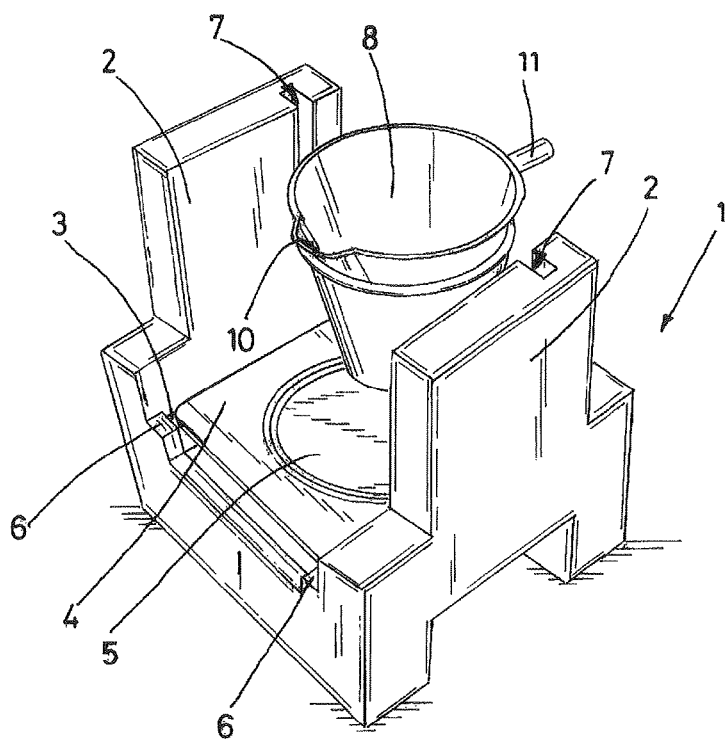
FIG. 1 is a top front perspective view of the apparatus according to the invention, including a crucible holder, a crucible, and a casting dish.
Figure 2:
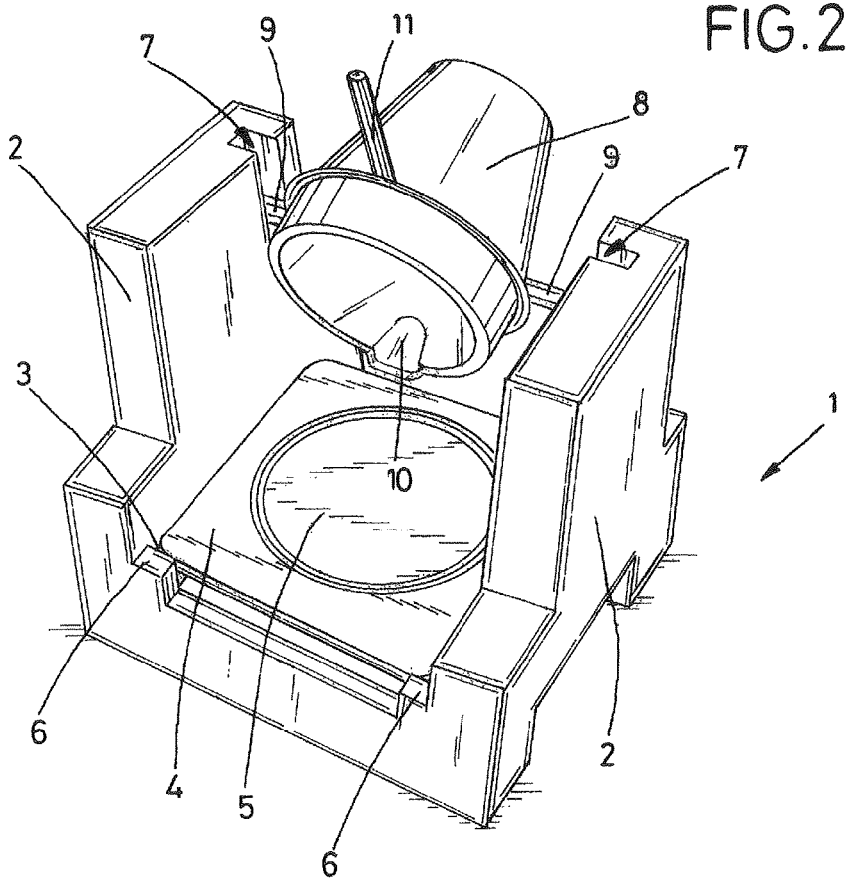
FIG. 2 is a front perspective view of the apparatus of FIG. 1, showing the crucible tilted.

FIGS. 1 and 2 illustrate a crucible unit 100 according to the invention that comprises a crucible holder 1, a crucible 8, and a casting dish support plate 4 with a casting dish 5. The construction of the crucible holder 1 is generally U-shaped with two side walls or crucible supports 2 that face each other and extend upward. A profile 3 extends horizontally along a lower portion on an inside face of each of the side walls 2 to form a narrow ledge, both of which serve as a support for the casting dish support plate 4.

The casting dish 5 is placed directly beneath the crucible 8. Preferably, the casting dish support plate 4 is locked into position in the crucible holder 1, to prevent it from shifting horizontally, so to ensure that the casting dish 5 is precisely beneath the crucible 8. There are numerous ways to secure the casting dish support plate 4, but creating a positive form-fit or locking fit between the crucible holder and the support plate is an effective way of locking the support plate 4 in position. For example, the support plate 4 may have a cut-out and/or a protrusion that extends along its circumferential edge, and the shape or geometry of the crucible holder 1 be such, that the support plate 4 is fitted into the crucible holder 1 with a positive locking fit that secures the support plate 4 and, thus, the casting dish 5 casting dish against horizontal movements relative the crucible holder 1. In the embodiment shown, the casting dish support plate 4 is a square or rectangular plate with the casting dish 5 in its center. Retaining noses 6 are formed in front and back lower edges of the crucible holder 1, at each end of the profiles 3. The side walls 2 and the noses 6 together provide a locking fit for the support plate 4 that prevents the plate from shifting in any horizontal direction. With this type of lock fit, the casting dish support plate 4 is simply set into the crucible holder 1 from above, so it is easy to load and unload from the crucible holder 1.

Positive lock-fit elements may also be achieved by providing two notches along the circumferential edge of the casting dish support plate 4, for example, the two notches opposite each other, and providing two extensions or elements on the crucible holder 1, such that two elements extend into the notches, thereby preventing a shifting of the support plate 4 in the crucible holder 1 in the horizontal plane. Several such positive lock-fit elements may be provided between the support plate 4 and the crucible holder 1. With these lock-fit elements, too, the casting dish support plate 4 is easily insertable into and removable from the crucible holder 1 simply by sliding it downward or upward along the notches, as the case may be.

Another means of providing the desired positive lock-fit may be achieved by providing the casting dish support plate 4 with a trough or hollow that extends into and mates with a corresponding recess or cut-out in the crucible holder 1.

The crucible holder 1 is shown only schematically, to sufficiently illustrate the essential components and surfaces that provide the desired functionality: tiltably supporting the crucible 8 in the crucible holder 1 and fixing the location of the casting dish support plate 4 in the crucible holder 1, such that the casting dish 5 is immovably located beneath the crucible 8.

It may be an advantage to use materials for the casting dish support plate 4 and the crucible holder 1 that have different thermal expansion coefficients, and to construct the two or more lock-fit elements with relatively large tolerances, to ensure that the casting dish support plate 4 doesn't stick in the crucible holder 1 and thereby interfere with its handling.

The crucible 8 is tiltably supported in the crucible holder 1 with the casting dish 5 placed directly beneath the crucible, so that, when tilted, the crucible 8 empties the crucible contents directly into the casting dish 5, as shown in FIG. 2. One embodiment of such a tilt mechanism is shown in the figures. Vertical recesses or grooves 7 are formed close to rear edges of and extend part of the way down the side walls 2. The crucible 8 has two juxtaposed protrusions 9 that are loosely captured in these grooves 7, so as to suspend the crucible 8 above the casting dish 5. It is understood that the illustrations are schematic in nature, and that the grooves 7 may be placed closer to the rear edge of the side walls 2. The two protrusions 9 form a straight axis that serves as a tilt axis for the crucible 8. It is understood, that the principle of this tilt mechanism may be exactly reversed, such that the crucible holder have protrusions that may be suspended in recesses that are formed in the crucible. The tilt axis about which the crucible 8 is rotated is then formed by the crucible holder protrusions supported in the recesses.

FIG. 1 shows the crucible 8 suspended in the crucible holder 1 in an orientation what would be used during the melting process when the sample material contained in the crucible 8 is being melted and FIG. 2 shows the crucible 8 tilted in a position to pour the molten crucible contents into the casting dish 5. The crucible 8 has an upper edge with a pour spout 10 is formed on one side of this upper edge and, juxtaposed to the pour spout, an extension 11 that extends horizontally from the upper edge of the crucible 8 and that serves as a handle to tilt the crucible. When the handle 11 is moved to a substantially vertical position, that the pour spout 10 then faces toward the casting dish 5.

The rather massive construction of the crucible holder 1, which can be seen in FIGS. 1 and 2, provides weight that makes the crucible holder very stable, so that, when the floor is moved in order to transmit motion to the crucible holder 1 and the crucible 8, to achieve the desired thorough mixing of the crucible contents, the crucible holder 1 is not likely to shift its position or topple. It is also within the scope of the invention to use a less massive design for the crucible holder 1, with a reduced amount of material. A lighter construction has the advantage that it requires less time and energy in the heating and cooling phases. The particular design of the crucible holder 1 will depend on the specific intended use.

The crucible holder 1 is constructed from a high temperature-resistant, high carbon content nickel-chrome-iron alloy. Such an alloy is commercially available under the trade name NICROFER from the company Krupp VDM GmbH. This alloy has proven durable at the temperatures that prevail in the oven. Surprisingly it has been found that, in conjunction with the material for the crucible 8, which in a conventional embodiment of a crucible is typically platinum, the alloy does not interact negatively with the material of the crucible, so that the crucible 8 may be used with this crucible holder 1 over an extended period time, i.e., for a number of trials, without a problem. The spatial weight of this metallic material is very high and this contributes to the high stability of the crucible unit 100, i.e., the crucible holder 1 along with its crucible 8, when both are moved together in the oven to mix the sample materials.

The crucible holder 1 may also be created from a different material, one that has a suitable resistance for the intended temperature loads. For example, ceramic materials may be used, particularly silicon nitride. Chemical resistance of the crucible holder 1 is important, because the temperature in the oven is very high and because the molten sample material may splash out of the crucible 8. Ceramic materials may possibly have a higher chemical resistance than do the metallic materials, and for this reason, may be advantageous.

The crucible holder 1 may also be constructed of a combination of different materials. For example, the lower portion of the crucible holder 1 may be constructed of a heavy material, to enhance stability, and the upper portion, in the direction of the crucible, of a more chemically resistant material, one which is not only resistant to the splashes from the crucible 8, but may also protect the lower portion of the crucible holder from splashes.

The crucible holder 1, along with the crucible 8 suspended therein, is placed loosely, i.e., without fastening elements such as latches or tie-downs, in a melting oven. The oven, the details of which are also not shown in the figures, has an enclosed inner chamber, whereby the floor has a movable portion which serves to impart motion to the crucible holder 1 and the crucible 8 for the purpose of mixing the crucible contents.

The crucible 8 is preferably constructed of a suitable material that is resistant to the high temperatures and that avoids unacceptable contamination of the sample, such as, for example, graphite, nickel, zirconium, or a ceramic material, or possibly graphite. In practice, an alloy that is 95% platinum and 5% gold has shown to have a long service life for doing X-ray fluorescence spectroscopy, and, although the materials are costly, the amounts are very small because of the small dimensions of a crucible, and, thus, the alloy has made analysis by X-ray fluorescence spectroscopy affordable. Other platinum alloys with admixtures of gold (in a different ratio than 5%), rhodium, iridium, palladium, etc., have also proven useful. In the embodiments shown, both the casting dish 5 and the crucible 8 are constructed of the platinum alloy and the casting dish 5 is an integral part of the casting dish support plate 4. It is understood, however, that the casting dish 5 may be a separate item that is fitted into the support plate 4.

No device or mechanism for actuating, i.e., raising, the handle 11 is arranged in the oven and, for that reason, none is shown in the drawings. A suitable actuating mechanism may be a robust construction with simple kinematics, such as, for example, a beam connected to or in contact with the underside of the handle 11. Moving the beam in an upward arc forces the handle 11 from the horizontal orientation shown in FIG. 1 to the approximately vertical orientation shown in FIG. 2. It is preferable that the beam be pushed into the oven when the sample material is already molten, so that the crucible 8 may remain in the oven while the crucible contents are emptied into the casting dish 5.

The tilt actuator, i.e., beam, may be constructed to withstand the high oven temperatures and be placed inside the oven, so that the molten sample material may be emptied immediately into the casting dish 5, without any temperature loss in the oven. This reduces the time the oven is open, because it is only opened for loading/unloading, and not for pouring, and this minimizes temperature losses in the oven.

A second possible method of tilting the crucible 8 is to place the tilt actuator outside the oven and to remove the crucible unit 100, i.e., the crucible holder loaded with the crucible and the casting dish, from the oven and to then tilt the crucible 8 to empty the sample material into the casting dish 5. The method substantially reduces the stresses that result from the high oven temperature, because the only exposure of the tilt actuator to high heat is the contact of the actuator with the crucible tilt handle 11.

A third possible method of tilting the crucible 8 combines the advantages of the first two methods, and that is to place the tilt actuator outside the oven, but to tilt the crucible 8 and empty the contents into the casting dish 5 while the crucible 8 is still inside the oven. To this end, the oven is opened and the tilt actuator moved into the oven. If the tilt actuator is the aforementioned beam, then the beam may be pushed into the oven, while the drive unit moving the beam remains outside the oven. The temperature losses of the sample material are kept low, because the sample remains in the oven. The temperature load on the tilt actuator is also relatively low, because it is inside the oven only briefly during the tilt operation and not during the entire duration of the melting process, so exposure to the high oven temperatures is brief. Also, it is possible that only certain parts of the tilt actuator are in the oven.

A fourth method of tilting the crucible 8 includes a tilt actuator with a two-part construction. For example, the above-mentioned beam may be movably supported inside the oven and may remain in the oven for the duration of the melting process. The relatively more complicated and more temperature-sensitive drive unit for the tilt actuator remains outside the oven. An actuating connection between the drive unit and the beam is created only when the crucible is ready for tilting, so that the beam may be lifted and the crucible tilted. A small opening in the oven may suffice to accommodate a connecting link between the beam and the drive unit, so that the temperature losses in the oven and on the sample material may be kept particularly low.

Figure 3:
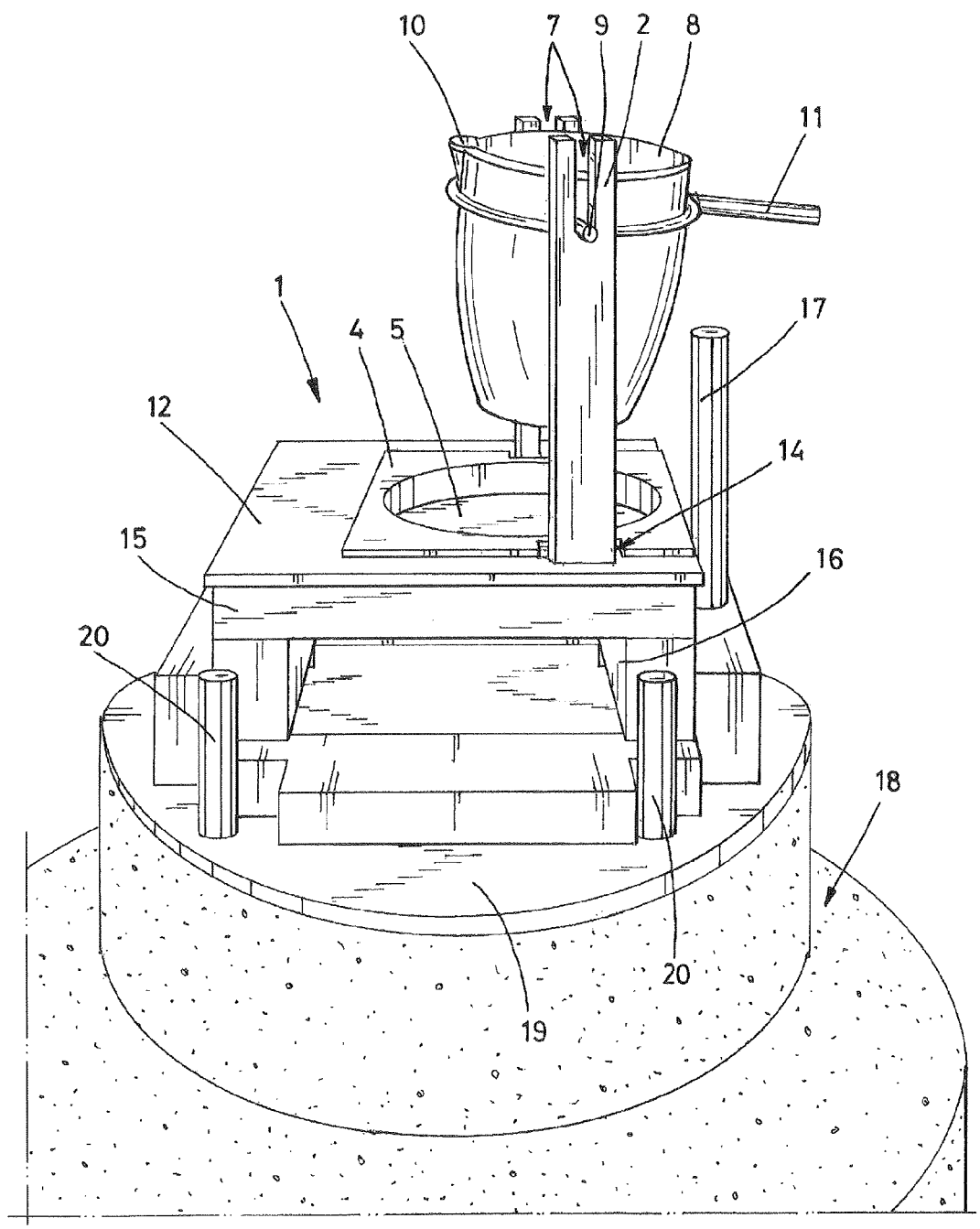
FIG. 3 is a view of a second embodiment of the crucible holder, mounted on a turntable.

FIG. 3 shows a second embodiment of the crucible unit 101 according to the invention, in combination with an oven floor 201 to form a movable oven floor and crucible unit 200. The crucible unit 101 comprises the crucible supports 2, the crucible 8, and the casting dish support plate 4 with casting dish 5 as described above, but has a platform 12 that supports the casting dish support plate 4 and has a cut-out to receive the casting dish 5. The crucible supports 2 of this crucible holder 1 are made of silicon nitride, as is the platform 12. The casting dish support plate 4 also has two notches 14 cut into it, one on each side, each notch 14 having a U-shape that fits around the respective crucible support 2, thereby providing a positive form-fit between the support plate 4 and the crucible supports 2 that prevents the casting dish support plate 4 from shifting in a horizontal direction. The crucible 8 may be removed from the grooves 7 in the crucible supports 2 simply by lifting it upward until the protrusions 9 are released from the grooves 7 and the casting dish support plate 4 may then also be easily guided upward and out of the crucible holder 1.

The crucible holder 1 is loosely placed on the oven floor, as mentioned above, but may be further secured against shifting by providing a profiled formation 21 on the oven floor that creates a form-fit for receiving the crucible holder 1 and prevents the holder 1 from shifting in any horizontal direction. The profiled formation 21 is assembled from multiple single components that are made of a conventional metal alloy known as "NICROFER". This alloy has good mechanical loadability, even at high temperatures, so that the crucible holder 1 may be repeatedly loaded into and unloaded from the oven, without creating unnecessary wear on the oven floor. The profile formation 21 has cut-outs at each of four corners and four ceramic pins 20 are inserted into the floor of the oven at these cut-outs and thereby prevent the profile formation 21 from shifting horizontally. These pins 20 may be removed, so that the profile formation 21 may be removed or replaced as necessary. The profile formation 21 is shown on a particular type of oven floor that is a turntable, to be discussed below, but it is understood that the same concept of securing the crucible holder on the oven floor may be used on a different type of oven floor.

Figure 4:
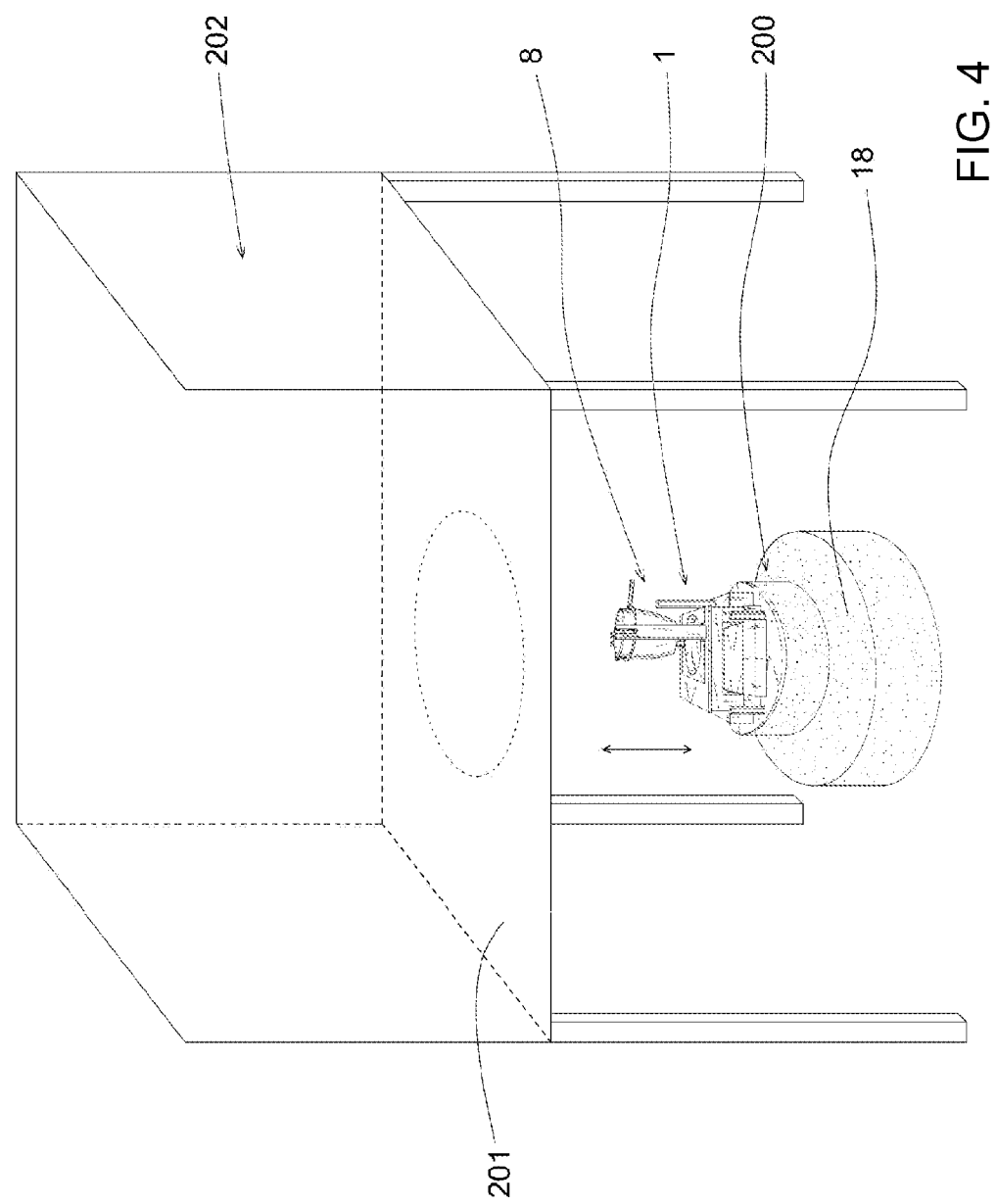
FIG. 4 is a schematic representation of a table-top oven with a turntable floor.

FIGS. 3 and 4 illustrate an oven 202 having an oven floor 201 that is constructed as a turntable 18. The oven 202 is shown purely schematically in FIG. 4 and the turntable shown in greater detail in FIG. 3. The turntable 18 is made of a thermally high-temperature-resilient ceramic base material, the same material that is used to line other areas of the oven, and has a stepped diameter, with the smaller diameter at the top. A cover plate 19 made of silicon nitride is provided on the upper face of the turntable 18. The cover plate 19 forms a protective layer that protects the ceramic base material from chemical loads, for example, against splashes from the sample material.

This turntable 18 provides an oscillating rotational motion. The repeated changes in direction of rotation enhance homogeneous mixing of the sample material contained within the crucible 8. The crucible 8 is shown in an off-center position relative to the center of the turntable 18 because this takes advantage of the increased centrifugal force at the outer edge of the rotating turntable 18, which further enhances the mixing effect. In other words, it is advantageous to place the tilt support for the crucible 8 as close to the edge in the crucible holder 1 as possible and to place the crucible holder 1 as close to the edge of the turntable 18 as possible, with the tilt support closest to the edge. In this way, the crucible 8 is placed as far away as possible from the rotational axis of the rotationally oscillating plate. In this off-center placement, the strongest possible forces work to achieve a thorough mixing of the sample material.

The turntable 18 may serve a dual function as the door to the loading opening in the oven. In this case, lowering the turntable to a "loading position" provides an opening that allows ready access to the inside of the oven for loading/unloading. The turntable 18 is shown in FIG. 3 in the lowered loading position, i.e., the turntable 18 has been pulled away from the oven, moved to the loading position, thereby creating an opening in the bottom of the oven that makes it possible to access the crucible holder 1, which is placed on the turntable 18. Once loading is finished, the turntable 18 is raised to its "operating position," in which it forms a part of the oven floor.

In the loading position, the opening may be kept to a minimum to allow loading/unloading of the crucible 8 and the casting dish support plate 4, but not opened wide enough to allow the entire crucible holder 1 to be removed from the oven. In this loading position, it is possible to load the crucible holder 1 with a fresh crucible and a fresh casting dish support plate 4 with the casting dish 5. The turntable 18 is subsequently moved up to its operating position.

The turntable 18 is also lowerable to a fully open position, in which the opening is large enough to allow the entire crucible unit 101 or the crucible holder 1 to be removed from the turntable 18.

The drive for the oscillating rotational motion of the turntable 18 may be placed outside the heated inner chamber of the oven. Also, an oven with a turntable floor allows for a mechanically robust construction of the entire apparatus, because it is not necessary to have a mechanical linkage between the crucible holder 1 and a drive means in the oven, in order to set the crucible holder 1 in motion and achieve the desired mixing motion of the crucible 8. For example, it is not necessary to connect a crank or mixing apparatus to the crucible holder 1, in order to apply a motion to the crucible holder 1 that is then transmitted to the crucible 8, to achieve the desired mixing effect on the sample material inside the crucible 8.

As is known, heated air moves upward, and loading crucibles 8 into the oven from below has the advantage that the heat generated in the oven is kept for the most part in the oven. Operating the oven in this manner is economically beneficial, because cooling losses are kept to a minimum when the oven is opened, and, as a result, the energy and the time for heating the oven back up to temperature is kept to a minimum.

Alternatively, rather than having a portion of the oven be movable, the entire oven may be set in motion, thereby setting the crucible holder 1 in the inner chamber of the oven in motion and, thus, the crucible 8 that is supported in the crucible holder. In so far as the oven has the appropriate vibration-resistant heating elements, such an oven that is set in motion from the outside is a mechanically simple construction. The term "oven" in this context includes the housing that surrounds the inner chamber of the oven and the heater that brings the inner chamber to the desired temperature. The external drive for such an oven is optimally protectible from the high oven temperatures. Placement of the crucible holder or holders 1 is preferably such, that the crucibles 8 in the holder or holders 1 are aligned in the same circular path, so that the same mixing conditions are exerted on all crucibles.

The crucible holder 1 has a sub-structure formed by upper bars 15 that extend in a direction that is labeled a "crosswise direction" and the two lower bars 16 that extend in a direction labeled a "lengthwise direction." The upper bars 15 may be provided instead by a solid plate 15. The upper bars 15 and lower bars 16 are made of the NICROFER material mentioned above. Splashes from the sample material attack silicon nitride much less than the NICROFER material, which itself is relatively robust. Particles that can possibly detach from the surface of the NICROFER components could, however, have a negative influence on the sample analysis, and for that reason the ceramic protective barrier of the plate 12 on the crucible holder 1, which is made of silicon nitride, is provided. The NICROFER material has a much higher volume weight compared to that of silicon nitride and, so, using NICROFER for the sub-structure lowers the center of gravity of the crucible holder 1 and thus increases its stability on the rotating turntable 18.

A lifting tool may be used to lift the crucible holder 1 along with the crucible 8 and the casting dish support plate 4. For example, a tongue or a fork of a lifting truck may be driven in a horizontal direction between the two lengthwise extending bars 16 and beneath the upper bars 15. The drive control that controls the rotational motion of the turntable 18 is designed such, that, when the turntable 18 is moved to its loading position, the turntable 18 takes a position at a pre-determined rotational angle and pre-determined height. This allows use of the lifting tool to be fully automated, because the pre-determined position of the turntable 18 ensures that the travel between the lower lengthwise extending bars 16 is unhindered.

FIG. 3 shows a vertical pin 17 mounted on the profile formation 21 that prevents the crucible 8 from tilting prematurely and emptying the crucible. If the full crucible 8 on the rotating turntable 18 starts to tilt as a result of the centrifugal force, then the stop 17 prevents this at an early uncritical stage. Raising the crucible holder 1 along with the crucible 8 and the casting dish support plate 4 moves the crucible 8 out of range of the stop 17.

The lifting tool previously mentioned may have an actuator that extends horizontally and parallel to the tongue or fork, and that reaches under the handle 11 of the crucible 8. The actuator may be part of a crank that is swingably mounted, for example swingable about a center of rotation that lies on the same axis as that of the two protrusions 9 of the crucible 8. By means of a motion in an upward swinging arc, the actuator guides the handle 11 upward and causes the crucible 8 to empty its contents into the casting dish 5 in the casting dish support plate 4.

The method according to the invention comprises placing sample material to be melted into a crucible and then supporting the crucible in the crucible holder, these steps done outside the oven, and then loading the crucible holder and crucible as a unit in the oven, whereby the crucible holder is loosely placed on the floor of the oven. The method further comprises placing a first crucible unit in the oven and, while it is undergoing the melting and pouring process, preparing a second crucible unit and after removing the first crucible unit from the oven, placing the second unit in the oven.

It is understood that the embodiments described herein are merely illustrative of the present invention. Variations in the construction of the crucible holder may be contemplated by one skilled in the art without limiting the intended scope of the invention herein disclosed and as defined by the following claims.

What is claimed is:

1. Apparatus for producing analysis samples for X-ray fluorescence spectroscopy, the apparatus comprising:
an oven constructed as a tabletop device and having an inner chamber that is heatable to at least 900 degrees C.;
a crucible for holding sample material to be melted, the crucible having a capacity of several cubic centimeters;
a crucible holder for holding the crucible; and
a casting dish for receiving molten sample material, the casting dish provided in the crucible holder beneath the crucible;
wherein the crucible is tiltably mounted in the crucible holder, such that the sample material in the crucible is pourable into the casting dish from the crucible by means of a tilt movement of the crucible; and
wherein the crucible holder is constructed with an inherent stability, such that the crucible holder is loosely placeable in the oven and, when a mixing motion is applied to the crucible holder to achieve a mixing of the sample material in the crucible, the crucible holder remains upright.

2. The apparatus of claim 1, wherein the oven is movably supported, so as to provide a mixing motion.

3. A crucible holder for X-ray fluorescence spectroscopy, the crucible holder comprising:
a base having two crucible supports, one crucible support extending upwardly from each of two opposing sides of the base and adapted to support a crucible that has a tilt axis; and
a casting dish support provided in the base for supporting a casting dish beneath the crucible, such that melted sample material in the crucible is pourable into the casting dish while the crucible is supported in the crucible holder;
a support plate that is adapted to receive the casting dish;
wherein the base includes one or more lock-fit elements that prevent the casting dish support plate from shifting in any horizontal direction.

4. The crucible holder of claim 3, wherein the crucible includes a crucible body for holding sample material and two protrusions that extend outward on juxtaposed positions on the crucible, so as to form the tilt axis, and wherein each of the two crucible supports has a recess for receiving one of the two protrusions, so as to tiltably support the crucible.

5. The crucible holder of claim 4, wherein the crucible supports are side walls and wherein the recesses are formed in the side walls, such that the crucible is placeable in the crucible supports simply by lowering the crucible so that the protrusions are held in the recesses.

6. The crucible holder of claim 4, wherein the crucible supports are posts and wherein the recesses are open grooves cut into the posts such that the crucible is placeable in the crucible supports simply by lowering the crucible so that the protrusions are held in the recesses.

7. The crucible holder of claim 3, constructed at least partially of a high temperature-resistant high carbon-content nickel-chrome-iron alloy.

8. The crucible holder of claim 3, constructed at least partially of ceramic material.

9. The crucible holder of claim 8, constructed at least partially of a material that contains silicon nitride.

10. The crucible holder of claim 3, wherein the casting dish support is formed by a profile provided on at least two sides of the base, and wherein the casting dish is supportable on the profile.

11. The crucible holder of claim 3, wherein the casting dish has a depression for holding the melted sample material and the support plate has a cut-out for accommodating the depression.

12. The crucible holder of claim 3, wherein the support plate has a depression and wherein the casting dish support has a corresponding depression, so that the support plate is securely held in the casting dish support, so as to prevent from shifting in any direction horizontally.

13. The crucible holder of claim 3, wherein the base includes a sub-structure formed by upper bars that extend in a crosswise direction and lower bars that extend in a lengthwise direction, so as to form a lifting space between the lengthwise bars and beneath the crosswise bars, the lifting space enabling a lifting tool to selectively lift and lower the crucible holder.

14. The crucible holder of claim 3, further comprising a vertical stop mounted on a rear side of the base and extending upward, the vertical stop preventing a premature tilting of the crucible.

15. A crucible unit for X-ray fluorescence spectroscopy, the crucible unit comprising:
- a crucible holder comprising a base having two crucible supports, one crucible support extending upwardly from each of two sides of the base;
- a crucible that is tiltably mounted in the crucible holder;
- a casting dish for receiving melted sample material from the crucible;
- a casting dish support provided in the base for supporting the casting dish beneath the crucible, such that melted sample material in the crucible is pourable into the casting dish while the crucible is supported in the crucible holder; and
- one or more lock-fit elements that prevent the casting dish support plate from shifting in any horizontal direction.

16. The crucible unit of claim 15, wherein the crucible has an actuating handle for tilting the crucible in the crucible holder.

\* \* \* \* \*